US006767341B2

(12) United States Patent
Cho

(10) Patent No.: US 6,767,341 B2
(45) Date of Patent: Jul. 27, 2004

(54) MICRONEEDLES FOR MINIMALLY INVASIVE DRUG DELIVERY

(75) Inventor: Steve T. Cho, Salinas, CA (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/880,377

(22) Filed: Jun. 13, 2001

(65) Prior Publication Data

US 2002/0193754 A1 Dec. 19, 2002

(51) Int. Cl.[7] .............................................. A61M 5/32
(52) U.S. Cl. ....................... 604/272; 604/272; 604/20; 604/273; 604/274
(58) Field of Search ........................ 604/20, 272, 274, 604/273; 606/167

(56) References Cited

U.S. PATENT DOCUMENTS

| | | | | |
|---|---|---|---|---|
| 3,633,580 A | * | 1/1972 | Knox | 128/347 |
| 3,645,268 A | * | 2/1972 | Capote | 128/347 |
| 5,250,067 A | * | 10/1993 | Gelfer et al. | 606/189 |
| 5,279,544 A | | 1/1994 | Gross et al. | |
| 5,457,041 A | | 10/1995 | Ginaven et al. | 435/172.1 |
| 5,486,547 A | * | 1/1996 | Matsuda et al. | 523/111 |
| 5,591,139 A | | 1/1997 | Lin et al. | 604/264 |
| 5,634,913 A | * | 6/1997 | Stinger | 604/272 |
| 5,899,915 A | * | 5/1999 | Saadat | 606/170 |
| 5,911,363 A | * | 6/1999 | Oligschlaeger | 239/11 |
| 5,968,022 A | * | 10/1999 | Saito | 604/272 |
| 6,033,928 A | | 3/2000 | Eriguchi et al. | 438/42 |
| 6,217,554 B1 | * | 4/2001 | Green | 604/164.01 |
| 6,312,612 B1 | * | 11/2001 | Sherman et al. | 216/2 |
| 6,334,856 B1 | * | 1/2002 | Allen et al. | 604/191 |
| 6,379,324 B1 | * | 4/2002 | Gerstein et al. | 604/22 |
| 2002/0082543 A1 | * | 6/2002 | Park et al. | 604/21 |

FOREIGN PATENT DOCUMENTS

| | | |
|---|---|---|
| WO | 99/64580 | 12/1999 |
| WO | 00/35530 | 6/2000 |
| WO | 01/33614 | 5/2001 |

OTHER PUBLICATIONS

K. Najafi, K. D. Wise and T. Mochizuki, "A High–Yield IC–Compatible Multichannel Recording Array," IEEE Micro. Trans. On Electron Devices, vol. ED–32, pp. 1206–1211, Jul. 1985.

* cited by examiner

*Primary Examiner*—Henry Bennett
*Assistant Examiner*—Camtu Nguyen
(74) *Attorney, Agent, or Firm*—Brian R. Woodworth; Michael R. Crabb

(57) ABSTRACT

The present invention provides a microneedle incorporating a base that is broad relative to a height of the microneedle, to minimize breakage. The microneedle further includes a fluid channel and a beveled non-coring tip. Preferably arrays of such microneedles are fabricated utilizing conventional semiconductor derived micro-scale fabrication techniques. A dot pattern mask is formed on an upper surface of a silicon substrate, with each orifice of the dot pattern mask corresponding to a desired location of a microneedle. Orifices are formed that pass completely through the substrate by etching. A nitride pattern mask is formed to mask all areas in which a nitride layer is not desired. A nitride layer is then deposited on the bottom of the silicon substrate, on the walls of the orifice, and on the top of the silicon substrate around the periphery of the orifice. The nitride layer around the periphery of the orifice is offset somewhat, such that one side of the orifice has a larger nitride layer. Anisotropic etching is used to remove a substantial portion of the substrate, creating a plurality of angular, blunt, and generally pyramidal-shaped microneedles. A subsequent removal of the nitride layer, followed by an isotropic etching step, softens and rounds out the blunt angular microneedles, providing generally conical-shaped microneedles. The uneven nitride layer adjacent the orifice ensures that the microneedles will include a beveled tip. Such microneedle arrays are preferably incorporated into handheld diagnostic and drug delivery systems.

13 Claims, 9 Drawing Sheets

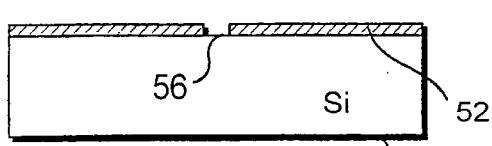
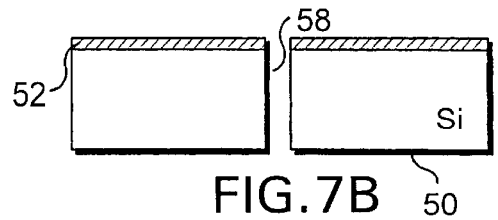
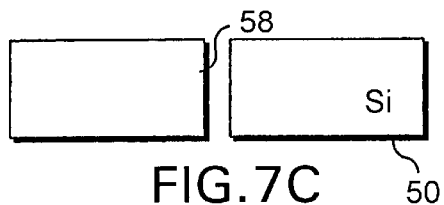
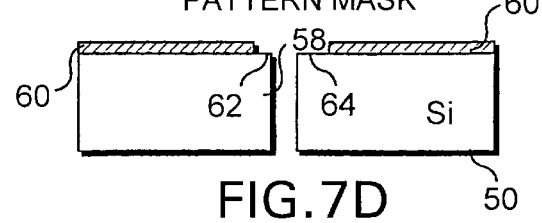
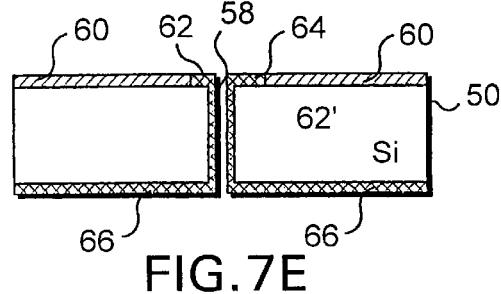
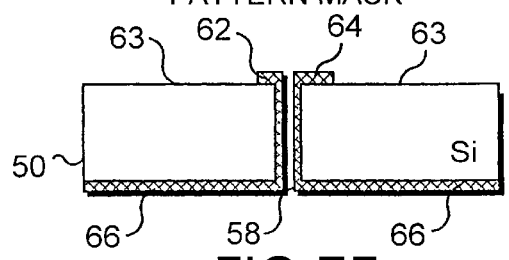
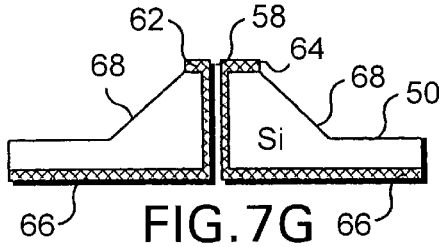
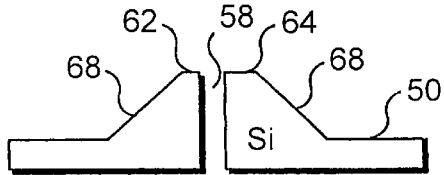
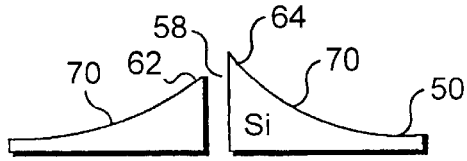
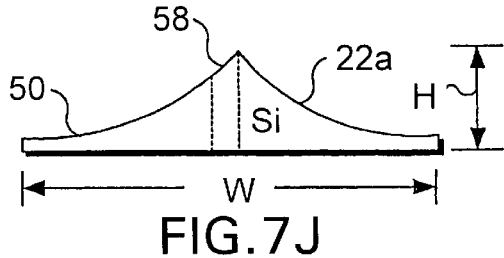

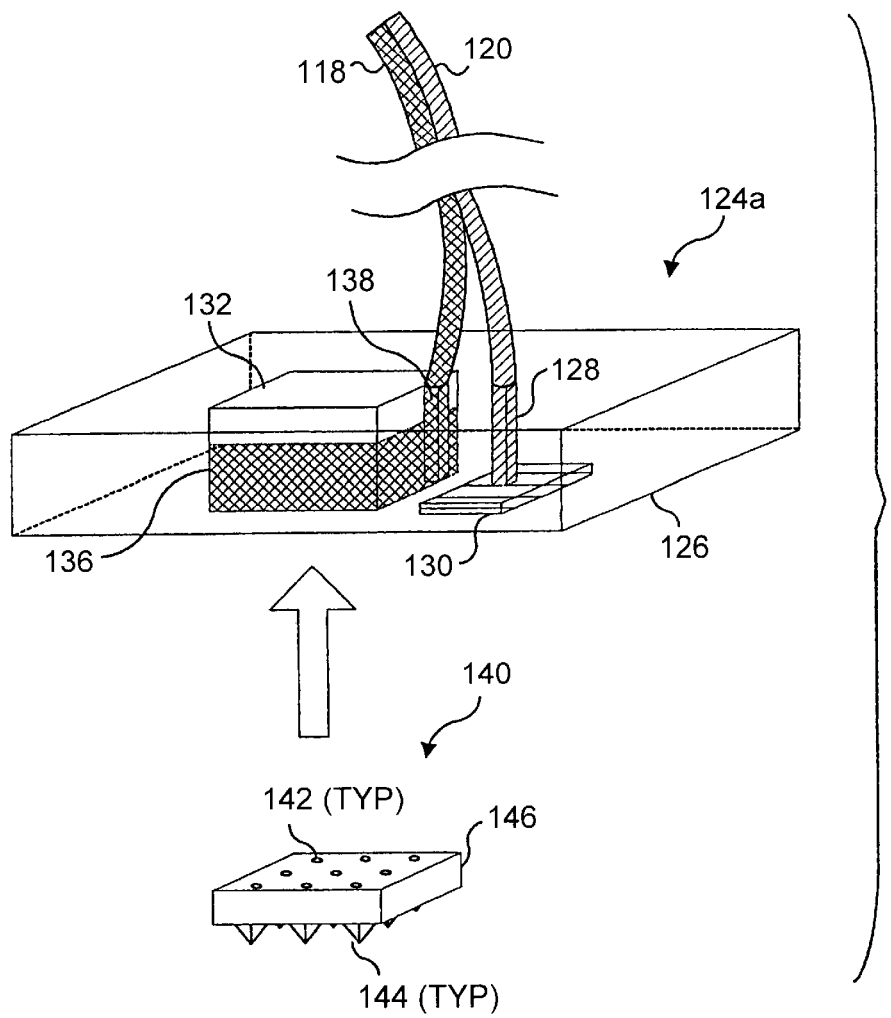
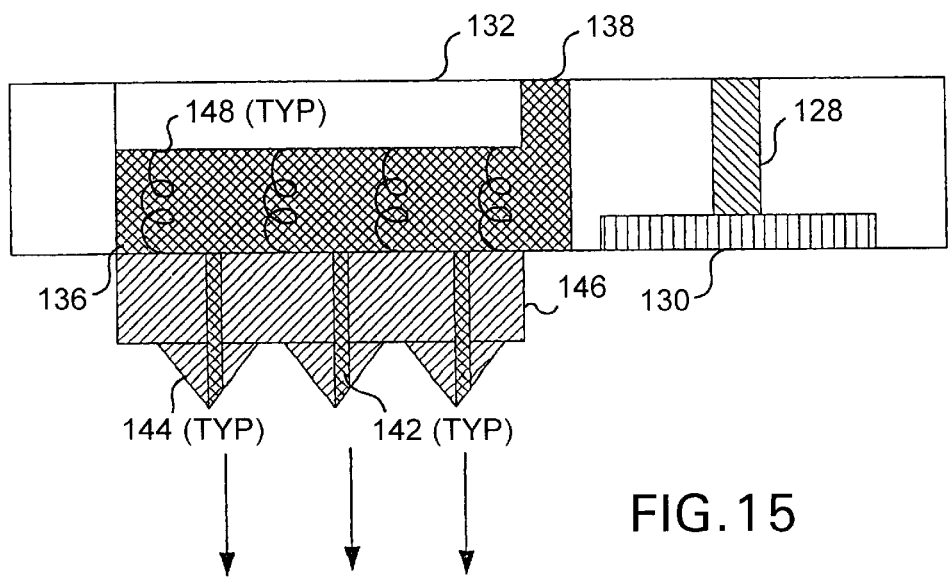

MICRONEEDLES FOR MINIMALLY INVASIVE DRUG DELIVERY

FIELD OF THE INVENTION

The present invention generally relates to apparatus used for delivering medicinal fluid to a patient, and a method for fabricating such apparatus, and more specifically, to apparatus having an array of microneedles for transdermally delivering a medicinal fluid to a patient in a minimally invasive manner, and a method for fabricating the same.

BACKGROUND OF THE INVENTION

There are many medical conditions and procedures in which it is necessary to either deliver a drug to a patient across the dermal barrier, or to withdraw a sample of blood or tissue from a patient across the dermal barrier. A hypodermic needle-tipped syringe is most commonly employed for transcutaneously delivering a medicinal fluid to a patient. A significant segment of the population considers receiving an injection delivered with a hypodermic needle to be a painful and unpleasant experience. Although most individuals are required to receive such injections only a few times over the course of their lifetime, those suffering from medical conditions such as diabetes will require much more frequent injections.

The size of the needle used with common hypodermic syringes is typically a few millimeters in length. These needles, which are referred to as macro-needles, have a relatively large diameter compared to the size of a biological cell. The pain associated with a needle piercing a dermal layer is clearly related to the diameter of the needle. In an attempt to decrease the level of pain an individual experiences when receiving an injection, the use of microneedles has been investigated. Microneedles can be fabricated in lengths that enable the dermal barrier to be penetrated sufficiently deep for drug delivery to occur, but not so deep as to stimulate nerves that cause pain and discomfort.

As an alternative to macro-needles, microneedles having a diameter measured in micrometers have been developed. The reduced size decreases discomfort and pain to the patient. Research has demonstrated that silicon microprobes with cross sections on the order of tens of micrometers can penetrate living tissue without causing significant trauma. (K. Najafi, K. D. Wise and T. Mochizuki, "A High-Yield IC-Compatible Multichannel Recording Array," IEEE Micro Trans. on Electron Devices, vol. ED-32, pp. 1206–1211, July 1985.)

Several different types of microneedles have been developed. Glass pipettes have been used to fabricate microneedles with a diameter of approximately 20 µm. These microneedles can be formed by heating a relatively large diameter glass pipette and stretching the pipette until its diameter is reduced to about 20 µm. Glass microneedles of this size can be used to inject and withdraw fluids from a single cell. However, the stretching technique employed to produce the microneedle is rather crude, and it is difficult to accurately and reproducibly control the size of a microneedle fabricated in this manner. Furthermore, such microneedles are extremely fragile.

U.S. Pat. No. 5,457,041 discloses an array of microneedles extending outwardly from a supporting substrate and having tip portions shaped and dimensioned to both carry a biologically active substance and to pierce and penetrate into target cells within tissue, so that the biological substance is transferred from the tip portion and deposited within the target cells. The array of microneedles is fabricated using silicon wafers and photolithographic-based etching techniques. The result is an array of solid microneedles. Any biologically active substance to be delivered by these needles must be loaded onto the tips of the microneedles to effect delivery. Such tip loading is not effective to deliver a precisely metered dose of a biologically active substance. Generally, medical treatment methodologies that include the transdermal injection of drugs into a patient require precisely controlling the amount of drug delivered. Delivery of too little amounts of a drug may not effect the desired result, and too much of the drug can have serious, possibly even fatal, consequences. Therefore, it would be desirable to provide a microneedle-based drug delivery system that offers better control over the dosage of the drug delivered by the microneedles, than this prior art technique.

U.S. Pat. No. 5,591,139 discloses a different type of silicon-based microneedle. Rather than producing an array of needles that extend outwardly from a substrate, this patent discloses fabricating a microneedle that extends parallel to the plane of a silicon substrate. Using a combination of masking and etching techniques, a hollow microneedle is formed, which includes an interface region and a shaft. A shell defining an enclosed channel forms the shaft, which has ports to permit fluid movement. The interface region includes microcircuit elements that can be used to provide micro-heaters, micro-detectors or other micro-devices on the microneedle. While a microneedle incorporating a fluid path is extremely useful, the shaft of the microneedle disclosed in this patent is relatively thin and narrow, and breakage is a concern. Furthermore, incorporation of electronic circuitry in the interface region increases the costs and complexity of these microneedles, and such circuitry is not required for all microneedle applications. Finally, using and manipulating an individual microneedle, as opposed to an array of microneedles, presents other challenges.

A more recent patent directed to microneedle arrays is U.S. Pat. No. 6,033,928, which discloses an array of semiconductor microneedles, each having a diameter sufficiently small to exhibit quantum effects. These semiconductor microneedle arrays can be used to provide a semiconductor apparatus with high information-processing functionality and are fabricated by forming a silicon dioxide film on a silicon substrate. Hemispherical grains made of silicon, each having an extremely small diameter, are then deposited on the film by vapor deposition. After annealing the hemispherical grains, the silicon dioxide film is etched using the hemispherical grains as a first dotted mask, thereby forming a second dotted mask comprising the silicon dioxide film. The resulting second dotted mask is used to etch the silicon substrate to a specified depth, thereby forming an aggregate of semiconductor microneedles. Note that drug delivery applications generally do not require a microneedle that is a semiconductor.

In consideration of the prior art discussed above, it would be desirable to provide an array of microneedles that each incorporate a fluid channel through which a controlled volume of fluid can be delivered. Preferably, such microneedle arrays would be designed to minimize the breakage of individual needles within the array, a common problem with prior art microneedles. It would be desirable to provide a method for fabricating such an array of microneedles that utilizes conventional micro-scale fabrication techniques, such that the size of the microneedles can be accurately and reproducibly controlled. It would be further desirable to provide a microneedle-based drug delivery system that offers full control over the dosage of the drug delivered by the microneedles. The prior art does not disclose or suggest such an apparatus or method.

SUMMARY OF THE INVENTION

In accord with the present invention, a hollow microneedle for transcutaneously conveying a fluid is defined. The microneedle has a generally conical-shaped body, with a beveled, non-coring tip that is able to pierce tissue and a broad base. A fluid channel extends through the body connecting the broad base in fluid communication with the tip.

Preferably, the height of the microneedle, which is the distance from the broad base to the tip, is the about the same or substantially less than a width of the broad base. The microneedle is fabricated from a silicon-based substrate, using semiconductor fabrication techniques.

In one embodiment, an array of hollow microneedles are fabricated. The array includes a substrate with at least one inlet and a plurality of outlets in fluid communication with the at least one inlet. The microneedles extend outwardly from the substrate, each being proximate to an outlet through the substrate. Each microneedle in the array is generally configured as noted above.

Another aspect of the present invention is directed to a method of manufacturing a hollow microneedle. The method includes the steps of providing a substrate; forming an orifice within the substrate, such that the orifice passes completely through the substrate; and removing a substantial portion of the substrate, leaving a remainder. The remainder is disposed around the orifice and is generally conical in shape, so that the orifice is disposed generally along a central axis of the conical shape. The step of removing a substantial portion of the substrate preferably bevels a tip of the conical shape.

In a preferred method, the substrate is silicon or polysilicon, and conventional semiconductor fabrication methods are employed for the fabrication process. For example, to form an orifice, a first mask is formed such that only portions of the substrate corresponding to a desired location of the orifice are exposed. The orifice is then etched, and the first mask removed. A second mask is formed and a nitride layer is deposited on unmasked areas. The second mask is then removed, and the substrate is etched to remove a substantial portion. The step of etching the substrate preferably comprises the step of performing an anisotropic etch, and then performing an isotropic etch.

Another aspect of the present invention is directed toward a method of manufacturing an array of hollow microneedles, which is generally consistent with the method discussed above.

Yet another aspect of the present invention is directed to a minimally invasive diagnostic system for sampling and analyzing a biological fluid from a patient. Such a system includes a handheld diagnostic unit, a disposable cartridge for obtaining a sample of the biological fluid, and a sensor that when in contact with the sample, produces a signal indicative of a characteristic of the biological fluid. The handheld diagnostic unit includes a housing, a processor, a display electrically coupled to the processor, a keypad electrically coupled to the processor, and a memory electrically coupled to the processor. The disposable cartridge includes a housing and an array of microneedles and is adapted to bring the sample into contact with the sensor.

Preferably, the memory stores machine instructions that when executed by the processor, cause it to perform a diagnostic procedure and indicate a result of the diagnostic procedure to a user on the display. In one embodiment, the diagnostic procedure determines a level of glucose in the biological fluid. Preferably, the housing includes a receptacle having a size and shape adapted to receive the disposable cartridge, such that when the cartridge is inserted into the receptacle, the sample of biological fluid is brought into contact with the sensor, and the sensor is electrically connected to the processor. In one embodiment, the sensor is disposed in the disposable cartridge, while in another embodiment, the sensor is disposed in the housing of the handheld diagnostic unit.

A still further aspect of the present invention is directed toward a minimally invasive drug delivery system for infusing a medicinal fluid into a patient. This system includes a handheld control unit, a disposable cartridge for delivering the medicinal fluid to the patient, and a fluid line connecting the handheld unit to the disposable cartridge. The handheld unit includes a housing, a processor, a display electrically connected to the processor, a keypad electrically connected to the processor, a memory electrically connected to the processor, a medicinal fluid reservoir controllably connected to the processor, a medicinal fluid outlet in fluid communication with the medicinal fluid reservoir, and an actuator that develops a pressure to force the medicinal fluid through the medicinal fluid outlet so that it is infused into a patient. The disposable cartridge includes a housing and an array of microneedles through which the medicinal fluid is infused into the patient.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIGS. 7A–7J are schematic representations of the sequence of logical steps used to fabricate a hollow microneedle in accord with the flow chart of FIG. 6;

FIG. 14 is a partially exploded view of a disposable cartridge that incorporates a microneedle array for use in the handheld drug delivery system of FIG. 12;

FIG. 15 is a side elevational view of the microneedle array used in the disposable cartridge of FIG. 14;

DESCRIPTION OF THE PREFERRED EMBODIMENT

Prior Art Microneedles

Figure 1A:
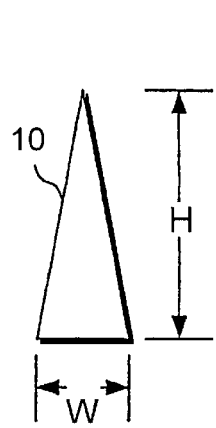
FIGS. 1A and 1B are side elevational views of prior art microneedles.
Figure 1B:
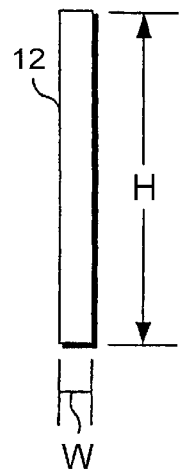

Before discussing the present invention, it will be helpful to consider several examples of prior art microneedles, generally with reference to FIGS. 1A and 1B. FIG. 1A shows a generally conically-shaped microneedle 10, having a width W, measured along its base, and a height H, measured from the base to the tip of the microneedle. Note that width W is substantially less than height H of microneedle 10, and that width W of the base corresponds to the diameter of microneedle 10 at its base.

A prior art microneedle (like microneedle 10) having a base whose width is approximately 30 µm and whose height is approximately 150 µm has been disclosed on the World Wide Web at the address http://mems.mirc.gatech.edu/research/biomed.html. Similarly, a microneedle having a base with a width ranging from 0.5 µm to 10 µm, and a height of approximately 100 µm is described in U.S. Pat. No. 4,969,468. This patent specifically teaches that the ratio of the height of the microneedle to the width of the base of the microneedle should be on the order of 10 to 1, resulting in a relatively slender microneedle. U.S. Pat. No. 5,457,041 discloses microneedles whose width at the base varies from 0.5 µm to 3.0 µm, and which are 10 µm to 25 µm tall. Each of these three sources thus disclose prior art microneedles whose height exceeds the width of their base by a ratio of at least 8:1.

FIG. 1B illustrates a generally cylindrically-shaped prior art microneedle 12, whose height H also substantially exceeds its width W, measured at its base. U.S. Pat. No. 6,033,928 discloses a microneedle shaped like microneedle 12, having a base whose width ranges from 0.002 µm to 0.05 µm, and whose height ranges from 0.5 µm to 2 µm. Thus, generally cylindrical microneedle 12 in the prior art have a height to width ratio of at least 4:1.

Figure 2:
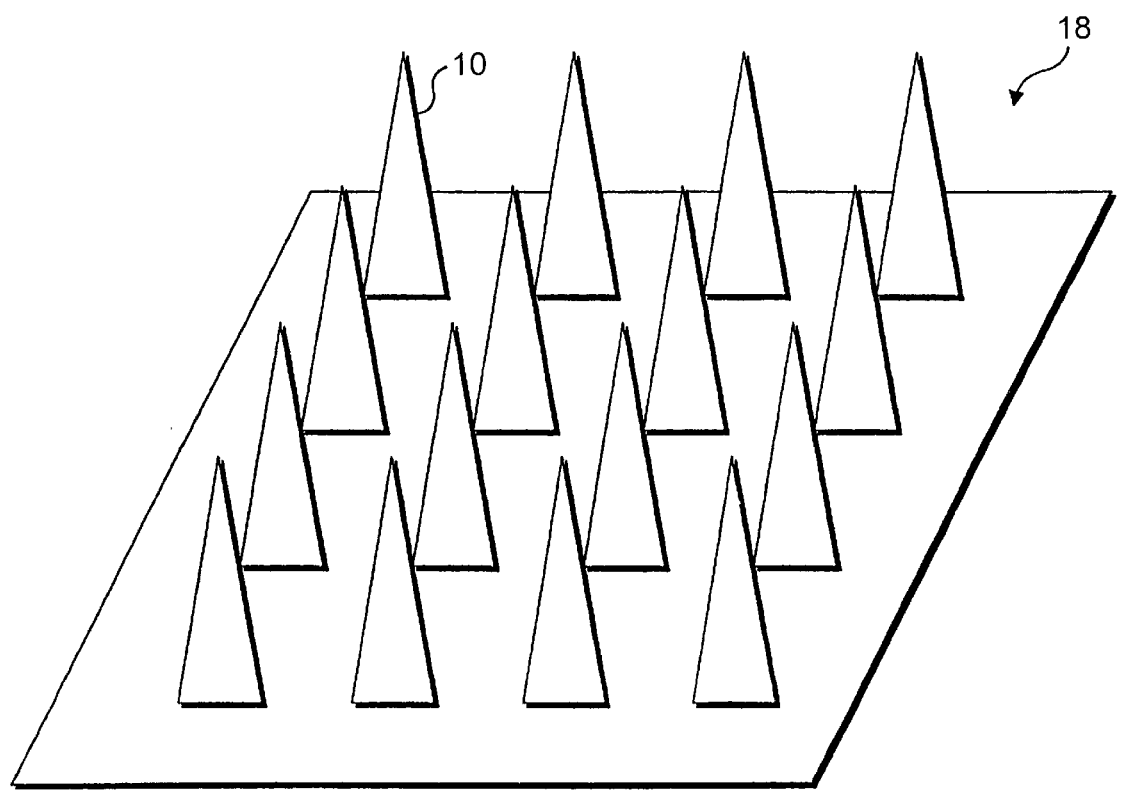
FIG. 2 is an isometric view of an array of prior art microneedles that can be fabricated using techniques common to semiconductor fabrication.

The microneedles of the prior art generally are fabricated of a silicon-based material using conventional semiconductor fabrication techniques. A prior art microneedle array 18 shown in FIG. 2 incorporates a plurality of prior art microneedles 10 from FIG. 1A. While other microneedles and arrays are disclosed in the prior art, their shape (height to base) characteristics are generally similar to those illustrated in FIGS. 1A, 1B, and to those shown in FIG. 2. Prior art microneedles generally tend to be slender "spike" or cylindrically-shaped structures whose height is substantially greater than their width at the base.

Microneedle of the Present Invention

Figure 3A:
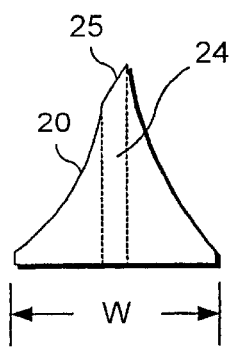
FIG. 3A is a side elevational view of a hollow microneedle in accord with the present invention.
Figure 3B:
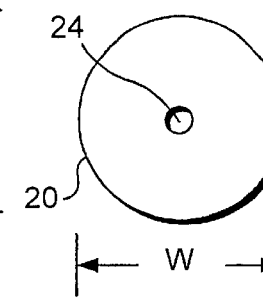
FIG. 3B is a plan view of the hollow microneedle of FIG. 3A.

FIG. 3A illustrates a microneedle 20 in accord with the present invention. In contrast to the prior art microneedles discussed above, microneedle 20 has a base whose width W is substantially equivalent to its height H. In one embodiment, the width and height are about 100 µm; however, it should be noted that this example is simply exemplary and is not intended to be limiting on the scope of the present invention. Microneedle 20 further incorporates a fluid channel 24 and a beveled, non-coring tip 25. FIG. 3B clearly shows that fluid channel 24 passes completely through the microneedle. Note that a ratio of height H to width W of microneedle 20 is substantially 1:1, whereas the microneedles of the prior art have height-to-width ratios ranging from 4:1 to 10:1. By insuring that the microneedles in the present invention have a base that is broad with respect to their height, a stronger microneedle, that is less prone to breakage, is provided.

Figure 4:
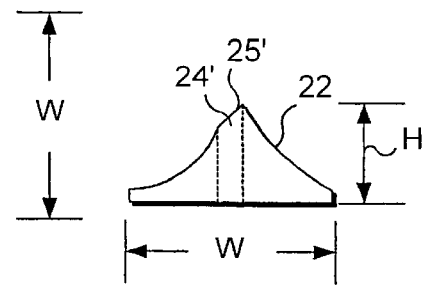
FIG. 4 is a side elevational view of another embodiment of a hollow microneedle in accord with the present invention, in which a base of the microneedle is substantially wider than a height of the microneedle.

FIG. 4 illustrates a second embodiment of a microneedle in accord with the present invention. Microneedle 22 incorporates a base whose width W exceeds its height H, i.e., its width W is approximately twice its height H. In one embodiment, the width W is about 100 µm, while the height H is about 50 µm, providing a height to width ratio of about 1:2. However, it should be similarly noted that the dimensions of 100 µm and 50 µm are simply exemplary, and are not intended to be limiting on the scope of the present invention. A key feature of microneedle 22 is that its ratio of height-to-width is less than 1:1, thus microneedle 22 has a base that is wider than its height. Microneedle 22 further incorporates fluid channel 24', and non-coring tip 25'.

Figure 5:
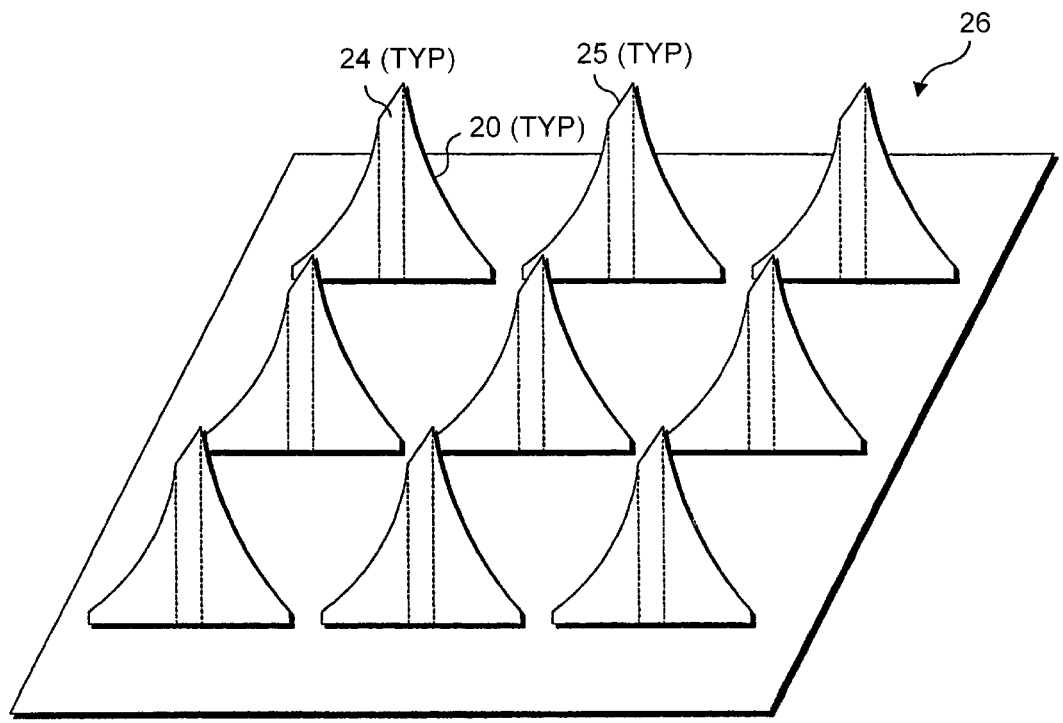
FIG. 5 is schematic view of a plurality of microneedles formed as an array, each microneedle in the array being like that illustrated in FIGS. 3A–3B.

FIG. 5 illustrates a microneedle array 26 of a plurality of microneedles 20. Each microneedle 20 in the array includes fluid channel 24 and non-coring tip 25, and each microneedle 20 has a height to width ratio of approximately 1:1.

Fabrication of Microneedle Array

Figure 6:
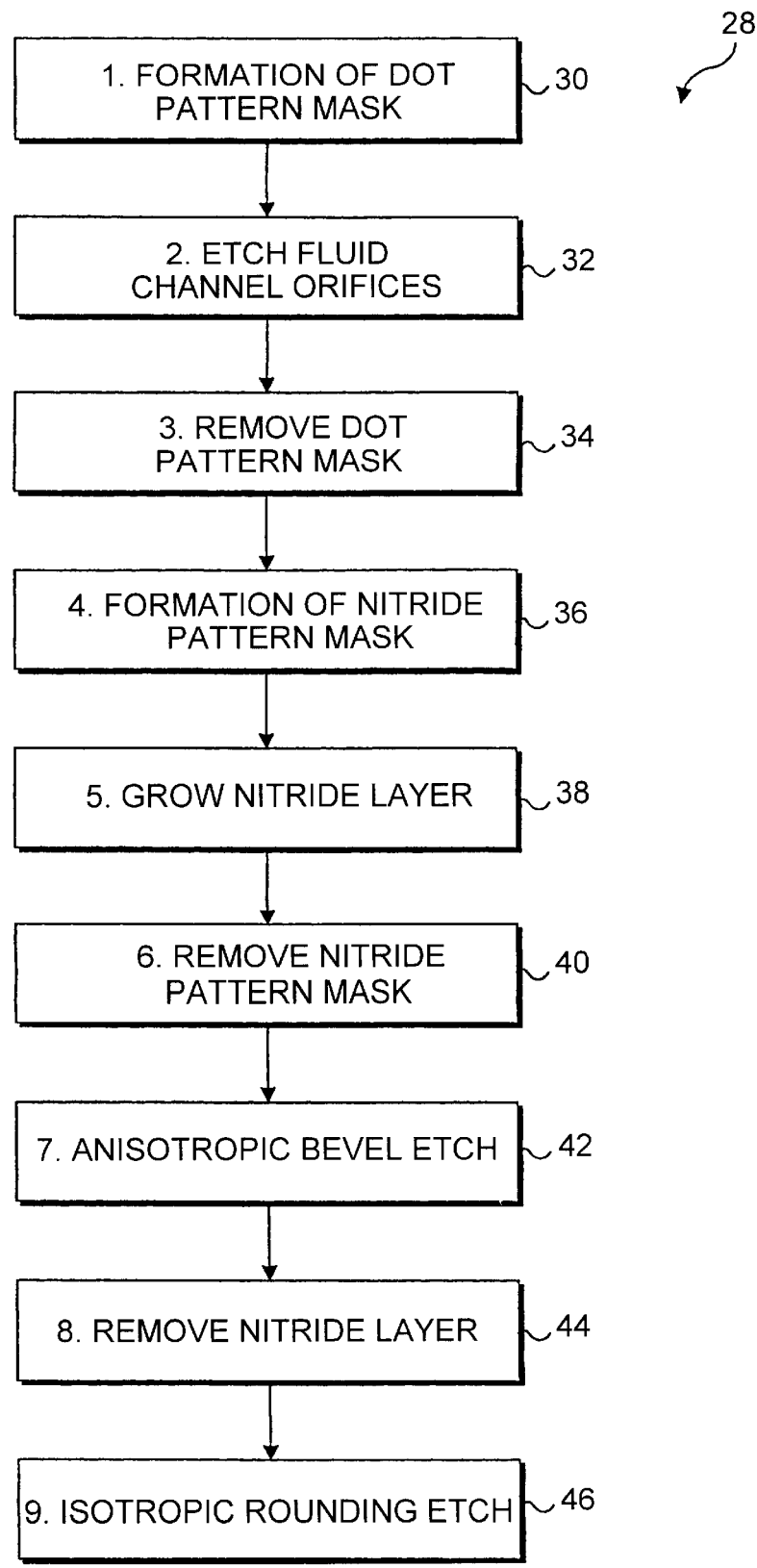
FIG. 6 is a flow chart illustrating the sequence of logical steps used to fabricate a hollow microneedle in accord with the present invention.

A flowchart 28 in FIG. 6 illustrates the sequence of logical steps used to fabricate a microneedle needle array in accord with the present invention. FIGS. 7A–7I illustrate cross-sectional views of a substrate material during the corresponding process steps in flowchart 28, while FIG. 7J illustrates a finished microneedle.

It is anticipated that photolithography and other techniques developed for use in the semiconductor fabrication industry can be beneficially employed in fabricating individual microneedles and arrays of microneedles in accord with the present invention. Thus, it is anticipated that silicon will be a preferred substrate, although other substrates, such as germanium, that can be manipulated using related techniques, might also be used. In general, an array containing a plurality of broad base microneedles is preferably manufactured in a batch process, following steps somewhat like those used in semiconductor manufacturing processes. Accordingly, a silicon substrate will typically comprise a four-, six-, or eight-inch silicon wafer on which a plurality of different microneedle arrays are fabricated at a time. However, for simplicity, fabrication of only a single microneedle is illustrated in FIGS. 7A–7J. In addition, it will be understood that the various layers comprising the microneedle are very thin, but for clarity, the dimensions of these layers as shown in the Figures are much exaggerated.

The following etching techniques are expected to be useful in fabricating microneedles in accord with the present invention. A Reactive Ion Etching (RIE) process is used to preferentially etch silicon oxide, silicon nitride, or a silicon substrate. For this purpose, a typical system includes a parallel plate reactive ion etching configuration with a 5 inch quartz electrode, and a 1 KW, 15 MHz radio frequency (RF) generator. Such a system can include a plurality of mass flow controllers, a throttle valve and a controller (to maintain constant pressure), and a high rate turbomolecular vacuum pump. RIE can be used to remove layers such as polyimide, silicon nitride, or silicon oxide from silicon substrates such as wafers, wafer pieces, or individual chips. Well known processes are available to etch silicon oxide and nitride (e.g., using carbon tetrafluoride, $CF_4$), to etch silicon oxide preferentially to silicon nitride (using $CF_4$ and fluoroform, $CHF_3$), and to etch silicon preferentially to silicon oxide (using silicon hexafluoride, $SF_6$).

A commercially available system such as that described above is the Cooke Vacuum Corporation, Model C71/3 Plasma System. Etch rates for most materials are 400–600 angstroms/minute. Etch rates for silicon oxide can be controlled to about +/−3%. The RF Frequency of the Cooke system is 14.56 MHz, and the RF power is variable, up to 1000 watts. Process pressures can range from less than 50 to more than 1000 mtorr. The upper and lower electrodes, which are quartz, are closed-circuit liquid cooled. Multiple gas mixing is available at the manifold.

In addition to RIE, wet etching can also be beneficially employed to perform the etching required to fabricate microneedles in accord with the present invention. Wet etching is a technique that utilizes liquid chemicals to remove materials surrounding a device or to delayer thin films from the surface of a substrate. This technique involves immersion of the device or substrate in a pure chemical or chemical mixture for a given amount of time. The time required is dependent on the composition and thickness of the layer to be removed, as well as the etchant and temperature. A succession of chemicals may be required to remove alternate layers on a device or substrate.

Wet etching can be used to remove organic materials, silicons, polyimides, metallization, polysilicon, or silicon oxide and silicon nitride layers. A few of the many chemicals available for etching include: hydrofluoric acid, hydrochloric acid, sulfuric acid, nitric acid, phosphoric acid, acetic acid, hydrogen peroxide, chromium trioxide, sodium hydroxide, potassium hydroxide, ammonium hydroxide, and ammonium fluoride. Etching time ranges from 30 seconds to 24 hours, depending on the etching temperature and the composition and thickness of the material to be etched.

Referring to FIG. 6, the logic starts at a block 30, in which a dot pattern mask is formed on a suitable substrate. As noted above, silicon is a preferred substrate material. FIG. 7A shows a mask 52 that is laid down on the upper surface of a silicon substrate 50. Mask 52 incorporates a round orifice 56. Orifice 56 is located in a position that corresponds to a desired location for a fluid channel in a microneedle that is being fabricated. Note that to fabricate an array of microneedles, a plurality of orifices 56 would be formed on a larger portion of substrate 50, each orifice corresponding to the location of a microneedle being fabricated on the substrate material. Regardless of the number of orifices 56 formed, the size (diameter) of the orifices in the dot pattern mask are about the same as that of the fluid channels in the finished microneedle array.

Mask 52 can be produced using standard photolithographic techniques, or using other masking techniques commonly used in the semiconductor industry. It is anticipated that mask 52 will be constructed by applying a layer of silicon dioxide onto silicon substrate 50, and then forming orifice 56 in the layer of silicon dioxide at the desired location.

Once the dot pattern mask has been formed, the logic moves to a block 32, and by etching the substrate where defined by orifice 56, as is illustrated in FIG. 7B, a fluid channel 58 is formed. Because the substrate is covered by the dot pattern mask in all areas except those areas defined by orifice 56, the only portion of the substrate that will be etched is the portion corresponding to the location of orifice 56. It is expected that a conventional bulk-machining etching process, such as wet etching using a potassium hydroxide (KOH) solution, can be beneficially employed. In such an etching process, the mask layer is much more resistant to the chemical used for etching than the substrate is, thus the substrate will be completely etched before the mask is removed. Preferably, the etching process will continue until the substrate has been etched completely through to form fluid channel 58, which passes completely through the microneedle and through the supporting substrate. However, it should be noted that the etching process could be controlled to a particular depth, if a fluid channel that does not completely pass through a substrate material is desired. Because the purpose of the fluid channel is to provide a fluid path between the tip of the microneedle and either a fluid supply or a fluid receiving reservoir (not shown here, see FIGS. 9 and 11), if the etching process does not completely etch through the substrate, an additional step would be required to complete the desired fluid path. It should also be noted that the RIE etching process described above can also be employed to etch the silicon substrate, while leaving the silicon oxide layer intact. Those of ordinary skill in the art will recognize that a plurality of other etching techniques can be beneficially employed in this step, and that the techniques noted above are simply exemplary of a preferred approach, and are not intended to be limiting on the scope of the present invention.

Once fluid channel 58 has been etched through the substrate, the logic proceeds to a block 34, and the dot pattern mask is removed. Removal of the dot pattern mask is the reverse of the etching process, because a chemical that dissolves the mask faster than it dissolves the substrate is used. Such mask removal techniques are well known in the art. FIG. 7C illustrates the result of this step, in which dot pattern mask 52, visible in FIGS. 7A and 7B, has been completely removed from silicon substrate 50.

The logic now proceeds to a block 36 in FIG. 6 and the fourth step, which is the formation of a nitride pattern mask. FIG. 7D illustrates this step, in which a nitride pattern mask 60 has been formed on silicon substrate 50. Note the areas of silicon substrate 50 in which no nitride pattern mask has been formed. Specifically, the nitride pattern mask is not formed on the internal surfaces of orifice 58, on the undersurface of silicon substrate 50, or on shoulder areas 62 and 64 around opening into fluid channel 58. In particular, note that shoulder area 62 on one side of the fluid channel is much smaller than shoulder area 64 on the opposite side. The significance of the difference in size between shoulder area 62 and shoulder area 64 will become clear below, from the discussion of subsequent steps in the fabrication process. It should be noted that this difference in the shoulder areas enables the formation of the beveled non-coring tip in the present invention. It is expected that a layer of silicon dioxide can be beneficially employed to form nitride pattern mask 60.

Once the nitride pattern mask has been completed, the logic proceeds to a block 38, in which a nitride layer is grown in all areas that have not been covered by nitride pattern mask 60. FIG. 7E illustrates the result of the nitride layer growth step, in which a nitride layer 66 is grown. Note that nitride layer 66 covers the undersurface of silicon substrate 50, shoulder areas 62 and 64, and the walls of fluid channel 58. One method of growing nitride layer 66 provides a 300–700 angstrom thick layer of nitride, using a low pressure chemical vapor deposition (LPCVD) of dichlorosilane ($SiH_2Cl_2$) in the presence of ammonia ($NH_3$), at a pressure of about ½ Torr and at a temperature of about 820° C. Those of ordinary skill in the art will recognize that other methods for fabricating nitride layer 66 can be employed and that the above noted technique is simply exemplary of one preferred approach, but is not intended to be limiting on the scope of the present invention.

After nitride layer 66 has been grown, the logic moves to a block 40 in FIG. 6, in which nitride pattern 60 is removed to expose those portions of silicon substrate 50 not covered with nitride layer 66. FIG. 7F illustrates silicon substrate 50, nitride layer 66, orifice 58, and shoulders 62 and 64. No mask or nitride layer covers areas 63 on the upper surface of silicon substrate 50. Areas 63 can be preferentially removed by etching, without removing the portions of substrate 50 covered by nitride layer 66. Note that nitride layer 66 at shoulders 62 and 64 mimics the offset pattern defined in nitride mask 60 of FIG. 7D.

After nitride pattern 60 is removed, the logic moves to a block 42 in FIG. 6, in which an anisotropic bevel etch is performed on areas 63. FIG. 7G illustrates the result obtained after this seventh step in the process. Those skilled in the art will understand that several different etching processes are available for use with silicon substrates. In particular, an anisotropic etch is characterized by the formation of sharp, angular boundaries. Anisotropic etching can be used to form trenches or side walls that are angular in shape, as opposed to the more rounded etching seen in an isotropic etching process. In anisotropic etching, the side walls etch much more slowly than the surface, resulting in sharp boundaries and enabling the formation of high aspect ratio structures. Tetramethylammonium hydroxide (N,N,N-Trimethyl-methanaminium hydroxide, or TMAH) is one of several etchants used to achieve anisotropic etching. Note that sharply defined, angular or beveled surfaces 68 have been formed into silicon substrate 50 of FIG. 7G. It should be noted that an anisotropic etch is also referred to as a "bevel" etch, while an isotropic etch is also referred to as a "rounding" etch.

The logic then moves to a block 42 in FIG. 6. In this block, nitride layer 66 is removed. As noted above, either RIE or wet chemical processes can be used to preferentially remove nitride layer 66. Furthermore, those of ordinary skill in the art will recognize that other methods of removing nitride layer 66 can alternatively be employed. FIG. 7H illustrates the result obtained after removing the nitride layer.

Finally the logic proceeds to a block 44, which indicates that an isotropic rounding etch is performed. Note that because nitride layer 66 has been removed, shoulders 62 and 64 are no longer protected. Thus, in the isotropic etching process, a portion of silicon substrate 50 at shoulders 62 and 64 is removed, forming the non coring tip of the microneedle, in accord with the present invention. As noted above, isotropic etching is characterized by forming rounded surfaces, such as curved surface 70, as opposed to the more angular surfaces formed in anisotropic etching.

FIG. 7J illustrates microneedle 22a as fabricated using the steps described in FIGS. 6 and 7A–7I. A ratio of a height H to width W of microneedle 22a is less than 1:2. Note that the size and shape of the original silicon substrate 50 in FIG. 7A can be manipulated to change the ratio of height H to width W in finished microneedle 22a of FIG. 7J. A thicker substrate 50 in FIG. 7A will result in a microneedle having a greater height H in FIG. 7J. Manipulation of the anisotropic etching step of FIG. 7G will also effect height H in finished microneedle 22a. A short etch time will result in a smaller height H, while a longer etch time will result in a greater height H.

Applications of the Microneedle Array

Figure 8:
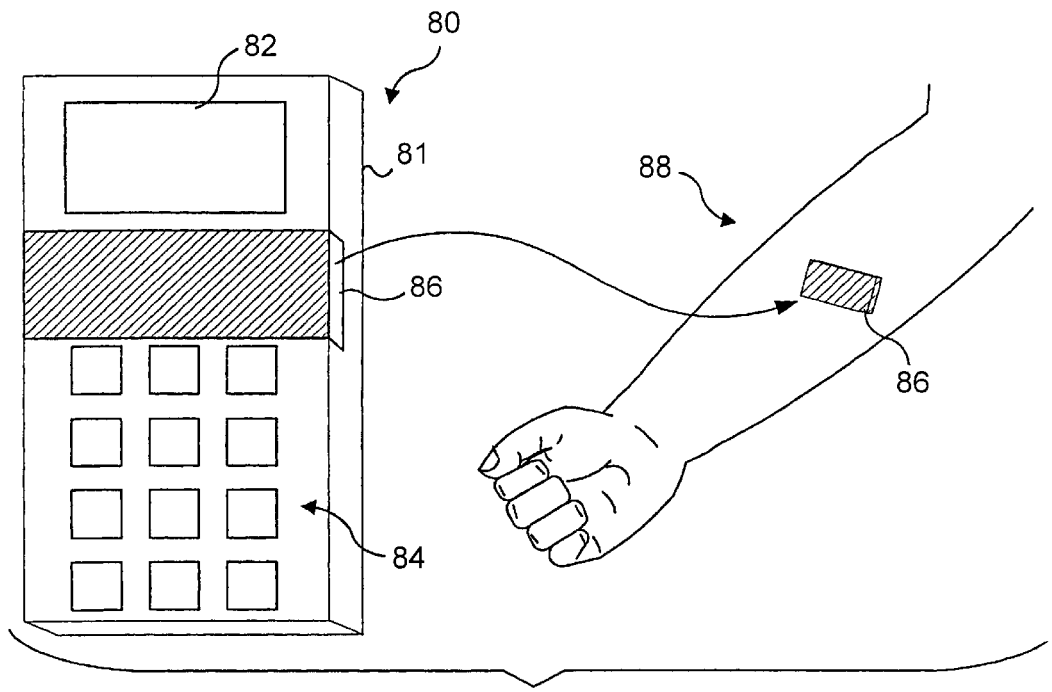
FIG. 8 is a schematic representation of a handheld diagnostic system that utilizes an array of microneedles in accord with the present invention.

Another aspect of the present invention is directed to the use of a microneedle array, configured as discussed above, in a diagnostic device. FIG. 8 illustrates such as a handheld diagnostic device 80. Handheld diagnostic device 80 includes a housing 81, a display 82, a keyboard 84, and a diagnostic cartridge 86. Note that diagnostic cartridge 86 can be removed from handheld diagnostic device 80. During use, diagnostic cartridge 86 is removed from handheld diagnostic device 80 and placed in contact with a portion of the user's skin, for example, on an arm 88 of the user. As explained below, blood is drawn from a patient's or user's body by the diagnostic cartridge for analysis in the diagnostic device, when the diagnostic cartridge holding the patient's blood is replaced in diagnostic device 80.

It will be noted that the terms "user" and "patient" are employed interchangeably throughout this specification and the claims that follow. It should be understood that the present invention can be employed my a user who is a medical practitioner to treat another person who is a patient, or a user who is a patient can directly employ the present invention.

Figure 9:
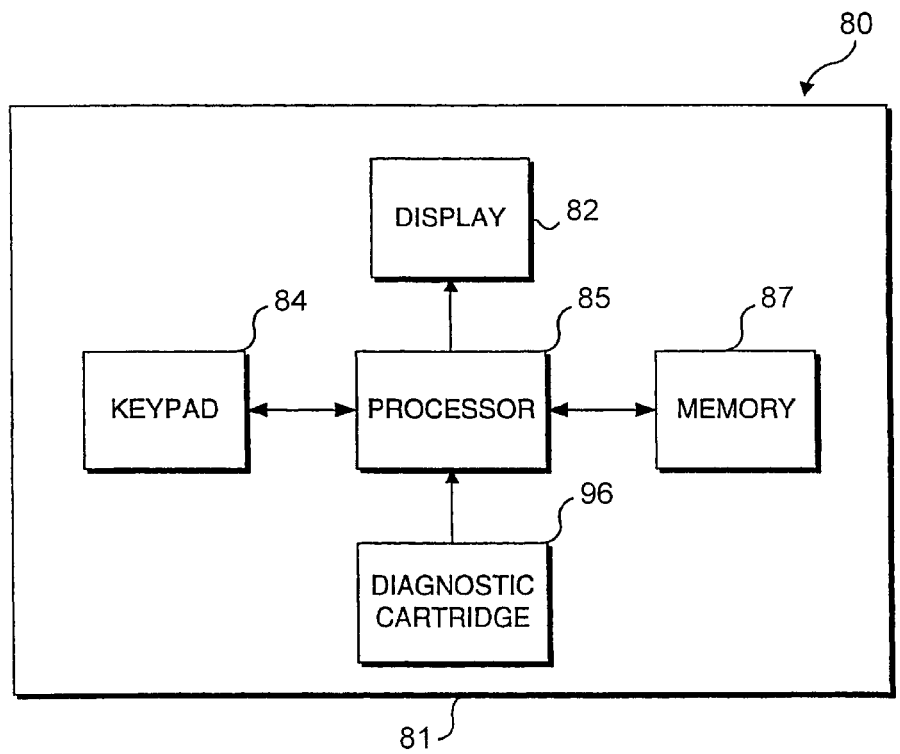
FIG. 9 is a block diagram showing the functional elements of the handheld diagnostic system of FIG. 8.

FIG. 9 illustrates additional functional elements of handheld diagnostic device 80 that are not visible in the schematic view of FIG. 8. A processor 85 is bi-directionally linked to a memory 87 and keypad 84. Display 82 is controllably connected to processor 85. Removable diagnostic cartridge 86, when properly inserted into housing 81, is electrically connected to processor 85, so that any data collected by diagnostic cartridge 86 are communicated to processor 85, which is programmed to run diagnostic routine on the signals provided by the diagnostic cartridge and to display the results on display 82. Preferably, memory 87 includes both read only memory (ROM) in which machine instructions are stored that cause the processor to carry out the diagnostic routine and display the results, and random access memory element (RAM) (neither type of memory separately shown). Memory 87 is bi-directionally coupled to processor 85.

Figure 10:
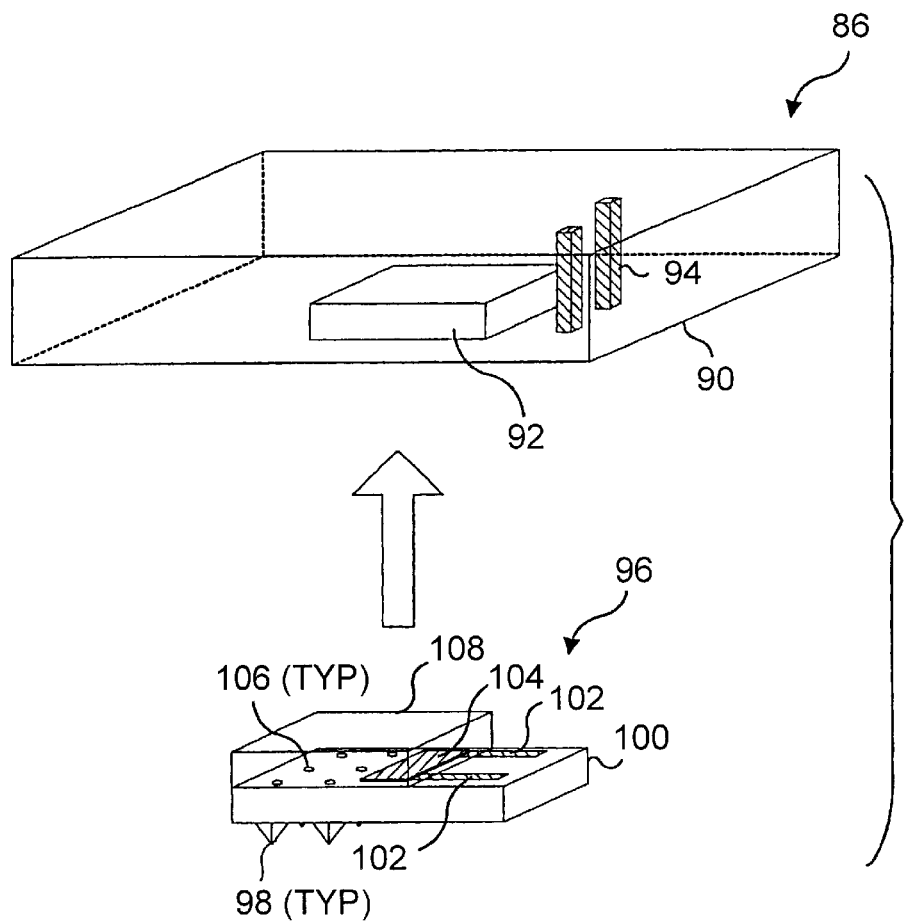
FIG. 10 is a partially exploded view showing a disposable cartridge that includes a microneedle array for use in the handheld diagnostic system of FIG. 8.

FIG. 10 illustrates further details of diagnostic cartridge 86. In FIG. 10, a diagnostic microneedle array 96 is shown exploded from diagnostic cartridge 86 to enable details of microneedle array 96 to be viewed, although it should be understood that in its fully assembled state, diagnostic microneedle array 96 is inserted into a cavity 92 of diagnostic cartridge 86. Diagnostic cartridge 86 includes a housing 90, a plurality of electrical conductors 94, and cavity 92.

Diagnostic microneedle array 96 includes a silicon substrate 100, onto which a plurality of microneedles 98 are formed. Note that each microneedle 98 has an associated fluid channel 106 that passes completely through substrate 100 as well as through the microneedle. As shown in FIG. 10, microneedles 98 are disposed on a bottom side of substrate 100. On an upper side of substrate 100, a sensor 104 and a plurality of electrical contacts 102 are disposed. Sensor 104 and electrical contacts 102 can be discrete components that are added onto substrate 100, but preferably, electrical contacts 102 and sensor 104 are formed using semi-conductor fabrication techniques onto the opposite side of silicon substrate 100 from microneedles 98. Electrical contacts 102 are positioned so as to contact electrical conductors 94 within housing 90. The configuration employed for sensor 104 is a function of the type of diagnostic procedure that diagnostic cartridge 86 is expected to perform and can be changed based on an intended usage. For example, one type of sensor that responds to glucose will be employed to determine the blood-sugar of a diabetic patient. Thus, a person having diabetes could employ handheld diagnostic device 80 and a diagnostic cartridge 86 designed to monitor the blood sugar level (measured in milligrams of glucose per 100 milliliters of blood).

FIG. 10 further illustrates a fluid reservoir 108 associated with diagnostic microneedle array 96. In one embodiment, fluid reservoir 108 is defined by the walls of cavity 92 in housing 90. In other embodiments, fluid reservoir 108 is defined by a separate plastic housing mounted on silicon substrate 100 and sized to fit within cavity 92.

Figure 11:
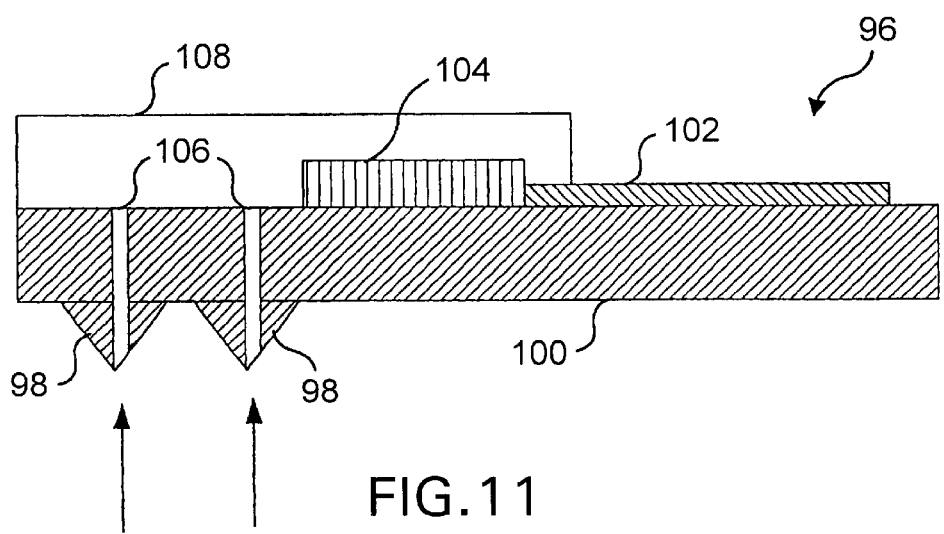
FIG. 11 is a side elevational view of the microneedle array used in the disposable cartridge of FIG. 9.

FIG. 11 illustrates a side elevational view of diagnostic microneedle array 96. Fluid channels 106 pass completely through both substrate 100 and microneedles 98. Fluid (such as a user's blood) is drawn up through these orifices into fluid reservoir 108 when the diagnostic cartridge is applied to the user's skin, as shown in FIG. 8. The fluid contacts sensor 104, and the electrical signals from the sensor are transmitted along electrical leads 102, which connect to electrical conductors 94 in diagnostic cartridge 86 when the diagnostic cartridge is inserted into cavity 92 of diagnostic cartridge 86.

In operation, a user will grasp diagnostic cartridge 86 and place it with microneedles 98 of diagnostic microneedle array 96 disposed adjacent the user's skin. The user would apply gentle pressure to diagnostic cartridge 86, enabling the microneedles 98 to pierce the user's dermal layer. A small volume of the user's blood would be drawn through fluid channels 106 into fluid reservoir 108. As the user's blood contacts sensor 104, electrical signals indicative of the parameters determined by sensor 104 are transferred from electrical contacts 102, to electrical conductors 94. The user then returns diagnostic cartridge 86 to handheld diagnostic device 80, and electrical conductors 94 connect to corresponding electrical contacts in the handheld diagnostic device, thereby transferring the sensor signal and the data they convey to processor 85. The signals provided to processor 85 are processed according to the machine instructions stored within memory 87. Results are displayed to a user via display 82. The user can employ keypad 84 to enter patient specific data that processor 85 may require to properly process the sensor signal data.

Figure 12:
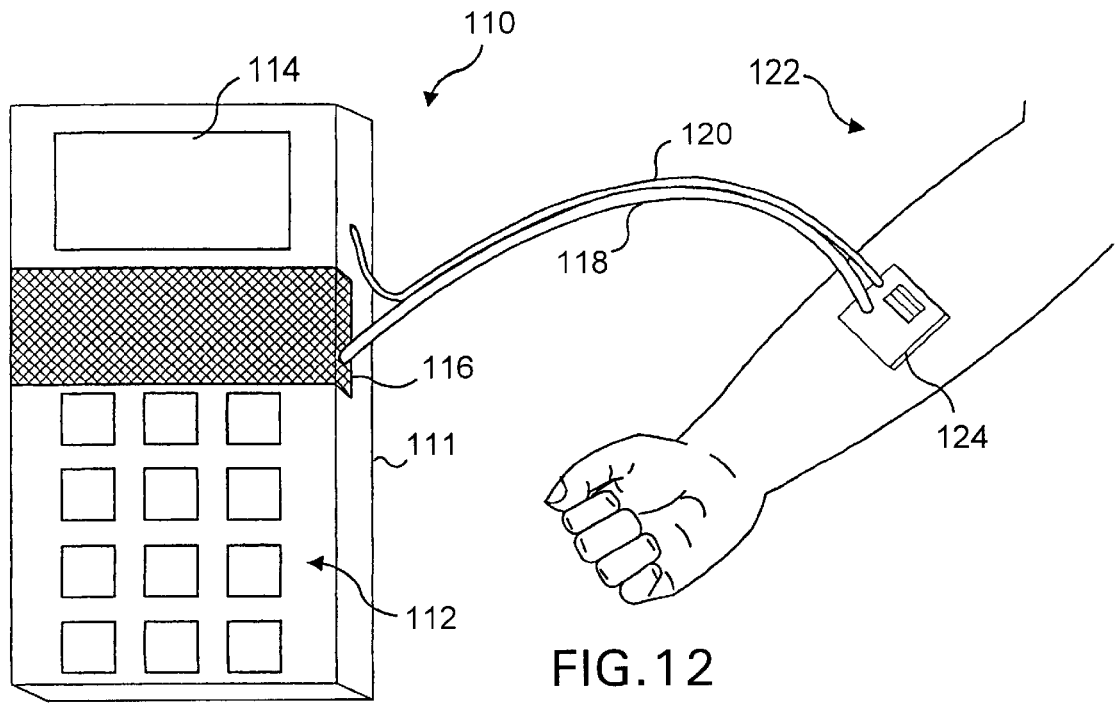
FIG. 12 is a schematic representation of a handheld drug delivery system that utilizes an array of microneedles in accord with the present invention.

FIG. 12 illustrates a handheld drug delivery unit 110 that includes many of the same components of diagnostic unit 80, which is shown in FIG. 8. It is expected that the same handheld unit will be used for both the diagnostic unit and the drug delivery unit. Handheld drug delivery unit 110 includes a housing 111, a display 114, a keypad 112, and a medicinal fluid supply 116 (which replaces diagnostic cartridge 86 in diagnostic unit 80 to provide handheld drug delivery unit 110). A fluid line 118 connects medicinal fluid supply 116 to a delivery cartridge 124, and an electrical line 120 connects handheld drug delivery system 110 to the delivery cartridge. A user will position delivery cartridge 124 so that it is disposed on the dermal layer (delivery cartridge 124 is illustrated disposed on an arm 122 of a user or patient) at a location to which the medicinal fluid is to be delivered.

Figure 13:
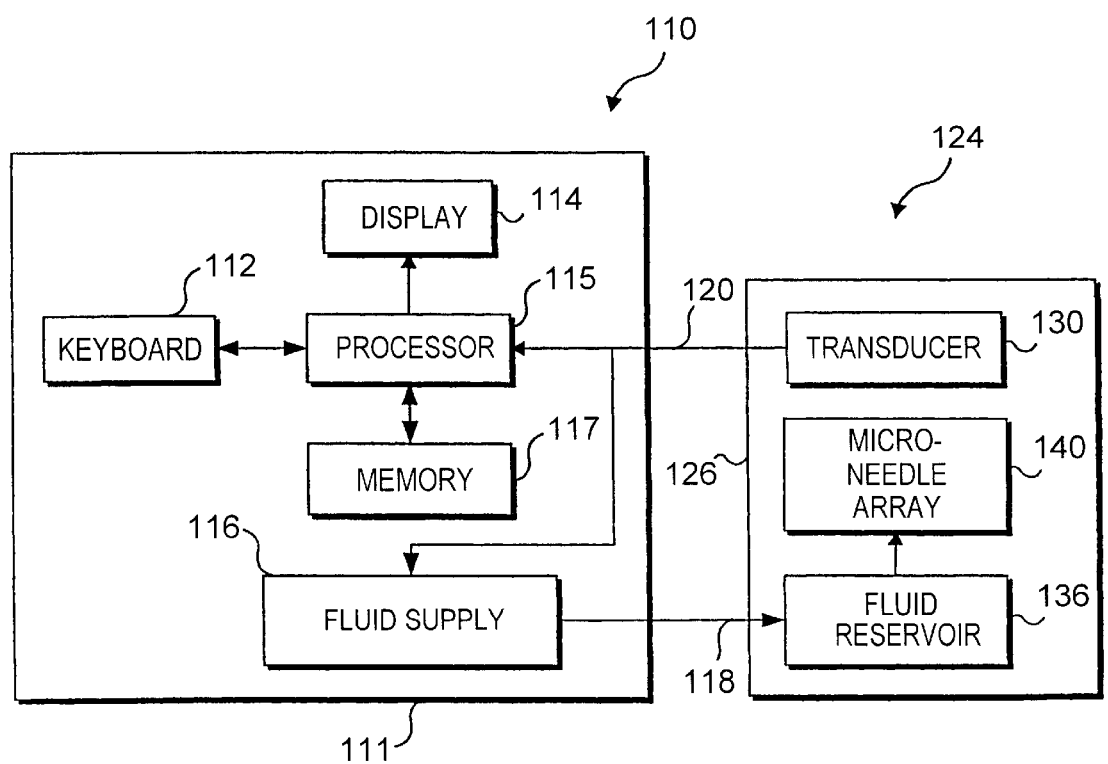
FIG. 13 is a block diagram showing the functional elements of the handheld drug delivery system of FIG. 12.

FIG. 13 illustrates additional functional elements of handheld drug delivery unit 110 and delivery cartridge 124 that are not visible in the schematic view of FIG. 12. A processor 115 is connected bi-directionally to a memory 117 and keypad 112. A display 114 is also connected to processor 115, as is fluid supply 116. Memory 117 includes ROM in which machine instructions are stored, and RAM. Delivery cartridge 124 includes a housing 126, a fluid reservoir 136 that is in fluid communication with fluid supply 116, and a transducer array 130 that is electrically connected to processor 115. Delivery cartridge 124 further includes a microneedle array 140 that is in fluid communication with fluid reservoir 136.

FIG. 14 illustrates a partially exploded view of a delivery cartridge 124a. Delivery cartridge 124a includes an additional element not present in delivery cartridge 124, which is a spring assembly 132 that produces a biasing force used to drive microneedle array 140 into a dermal layer with a force sufficient to enable microneedles 144 to pierce the patient's or user's dermal layer. FIG. 14 also illustrates details showing how transducer array 130 is electrically coupled to handheld drug delivery system 110, and how fluid reservoir 136 is connected in fluid communication with handheld drug delivery system 110. Delivery cartridge 124a includes electrical contacts 128, which connect ultrasonic transducer 130 to electrical line 120. The electrical line is connected to processor 115 of handheld drug delivery system 110. A fluid passage 138 is in fluid communication with fluid reservoir 136 and also in fluid communication with a fluid line 118 that connects with fluid supply 116 of handheld drug delivery system 110.

Spring assembly 132 is mounted on an upper portion of housing 126, directly over fluid chamber 136. Microneedle array 140 is designed to fit within fluid chamber 136. FIG. 12 shows microneedle array 140 exploded away from delivery cartridge 124a so that details relating to microneedle array 140 can more clearly be seen; however, the microneedle array is designed to be mounted within housing 126 under normal circumstances. Microneedle array 140 includes a silicon substrate 146 on which the plurality of microneedles 144 are formed. A plurality of orifices 142 pass completely through substrate 146 as well as microneedles 144. As noted above, other materials, such as germanium, can be used for the substrate.

FIG. 15 illustrates further details of microneedle array 140. In this view, orifices 142 can clearly be seen passing completely through substrate 146 and microneedles 144. A plurality of springs 148 connect substrate 146 to spring assembly 132 and are adapted to apply a biasing force that enables the microneedles to pierce the dermal layer, when the springs are compressed and then suddenly released to expand, applying a biasing force directed against the microneedle array, while the microneedle array is in contact with a user's skin. Fluid chamber 136, fluid passage 138, and orifices 142 cooperate to deliver a medicinal fluid to a user. Note that FIG. 15 illustrates microneedle array 140 and springs 148 in an extended position.

In an alternative embodiment that does not include spring assembly 132 and springs 148, microneedle array 140 is instead fixed within the delivery cartridge, and the delivery cartridge positioned with the microneedles disposed against the user's dermal layer. The penetration of the user's dermal layer can then be achieved by merely applying sufficient manual pressure against delivery cartridge 124.

Figure 16:
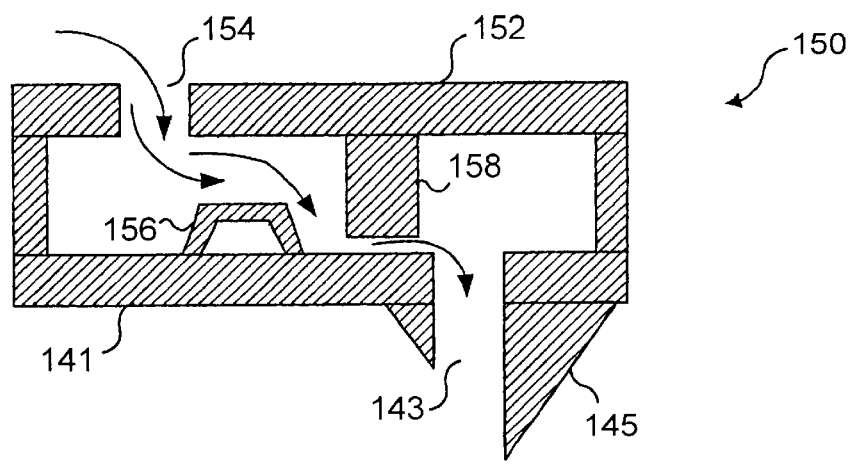
FIG. 16 is a schematic representation of a portion of a microneedle element for use in the handheld drug delivery system of FIG. 12, illustrating a fluid path within the element.

FIG. 16 illustrates a microneedle element 150 that includes a flow sensor 156 and a flow control valve 158. Microneedle element 150 can be used in place of microneedle array 140 in delivery cartridge 124 or 124a. Microneedle element 150 includes a substrate 141, a fluid channel 143, and microneedle 145. While for simplicity, only a single microneedle and orifice are illustrated, it should be understood that a plurality of microneedles and fluid channel can be beneficially incorporated into microneedle element 150. If a plurality of microneedles and fluid channels are included, then either a plurality of sensors and flow control valves (one for each microneedle) should be included, or sensor 156 and flow control valve 158 should be sized sufficiently large to effect the flow of fluids in the range required for the plurality of microneedles. For instance, if microneedle element 150 is incorporated into an array of microneedles, then a single sensor and a single flow control valve having widths as least as wide as a width of the array may be required.

Flow sensor 156 can be separately fabricated and attached to substrate 141, or traditional semi-conductor manufacturing techniques can be used to fabricate flow sensor 156 on substrate 141. Preferably, housing 152 is fabricated from silicon as well, such that traditional semi-conductor manufacturing techniques can be used to fabricate flow control valve 158. However, other manufacturing techniques may be employed. An orifice 154 is disposed in an upper portion of housing 152 to enable a medicinal fluid to enter microneedle element 150.

Figure 17:
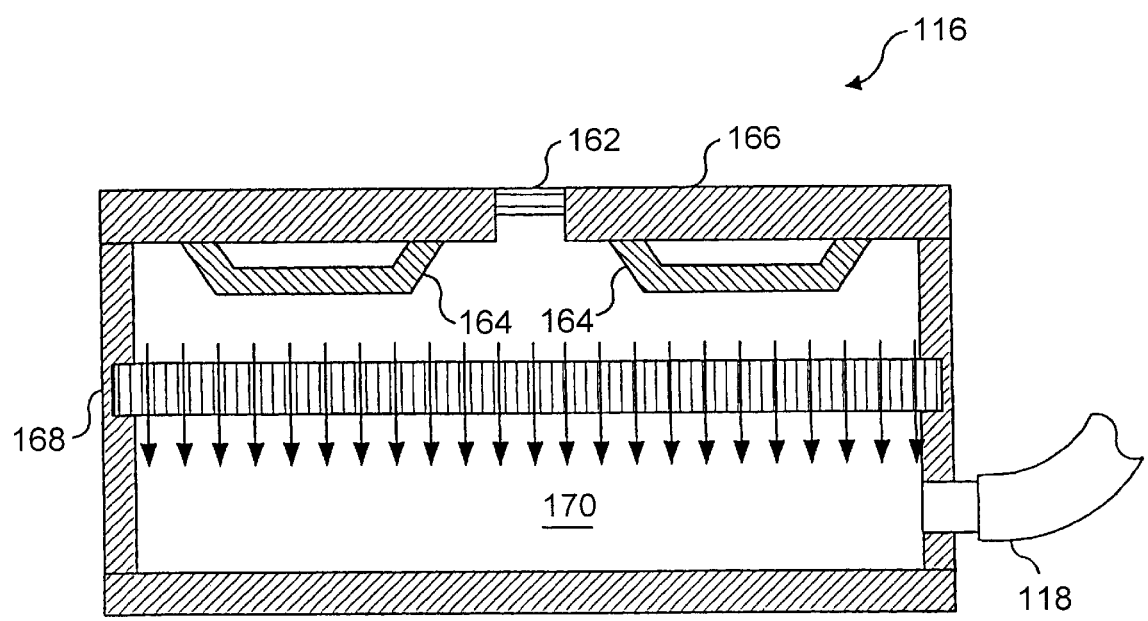
FIG. 17 is a schematic representation of a drug reservoir for use in the handheld drug delivery system of FIG. 12, illustrating a self-sealing membrane, two actuators, and a sub-micron filter.

FIG. 17 provides additional detail of an embodiment of fluid supply 116. As illustrated in FIG. 12, fluid supply 116 is disposed in handheld delivery system 110. It is envisioned that fluid supply 116 can be a disposable unit that is replaced once the medicinal fluid contained within is fully dispensed. Fluid supply 116 preferably includes an upper housing 166, a plurality of electromechanical actuators 164, a self-sealing elastomeric membrane 162, and a sub-micron filter 168.

Electrochemical actuators are know in the art. Such actuators apply a voltage to a fluid in a sealed chamber. The voltage causes the fluid to generate a gas, which in turn increases the pressure within the chamber, thereby providing the desired mechanical actuation force. When the voltage is removed, the gas is reabsorbed by the fluid, which can then be electrically stimulated to repeat the process, as desired. Some electrochemical actuators employ a fluid, which reversibly oxidizes in response to the application of a voltage, and when the voltage is removed the corresponding reduction reaction returns the fluid to its original state.

To fill fluid supply 116, a syringe (not shown) pierces self-sealing elastomeric membrane 162, so that the medicinal fluid can be injected from the syringe into an interior of fluid supply 116. When actuators 164 are providing no driving pressure to the fluid within the interior of fluid supply 116, the fluid will not pass through sub-micron filter 168. However, when an appropriate actuation pressure is provided by actuators 164, the fluid will pass through sub-micron filter 168 and into chamber 170, flowing into fluid line 118.

In general, when a user is ready to use drug delivery system 110, the first step would be to insure that the desired medicinal fluid supply 116 is inserted into unit 110. It is anticipated that a single user might use drug deliver system 110 to administer more than one type of medicinal fluid, and that such a user would have a plurality of medicinal fluid supplies 116 containing different types of medicinal fluids. The user would then enter user data, such as the desired delivery rate, using keypad 112. Using such information, processor 115 can control the delivery rate, by controlling the fluid flow from fluid supply 116. In a preferred embodiment, processor 115 controls the pressure delivered by actuators 164, to provide the desired fluid delivery rate. The user will position delivery cartridge 124 on a desired portion of the user's dermal layer. Generally, this portion will be on the arm of the user, or patient, although other portions of the patient's dermal layer can be used for transcutaneously infusing medicinal fluids.

With reference to FIG. 15, an ultrasonic transducer array 130 is included to enable a particularly desirable target location to be selected. Ultrasonic transducer 130 transmits ultrasonic signals into the patient's body, receives the reflected signals, producing corresponding signals indicative of the internal structure, and conveys the signals to handheld delivery system 110 via electrical line 120. Processor 115 monitors the signals from transducer array 130, and once a desired location has been achieved as the user moves delivery cartridge 124 across the user's skin, processor 115 causes display 114 to alert the user that delivery cartridge 124 is in a desired position. At this point, either by using a light pressure to force microneedles 144 through the dermal layer, or by employing springs 148 to drive the microneedles through the dermal layer, delivery cartridge 124 begins to deliver a controlled amount of medicinal fluid to the patient across the dermal barrier. The appropriate position can be determined based upon the characteristics of the patient's skin, or based upon the internal condition of the patient's body. For example, it may be appropriate to use the ultrasonic transducer to determine a position on the dermal layer that is adjacent injured internal soft tissue, so that a pain killer and/or anti-inflammatory can be injected into patient at that site using delivery cartridge 124.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A hollow microneedle comprising:
   (a) a generally conical-shaped body having a beveled, non-coring tip, said tip being sharp and able to pierce tissue;
   (b) said conical body further having a broad base formed of a substrate at an opposite end from the tip; and
   (c) a fluid channel extending through the conical-shaped body, providing fluid communication between said broad base and said tip;
   (d) wherein the body has a concave curved surface defined adjacent the tip.

2. The hollow microneedle of claim 1, wherein a height of the microneedle, which is defined as a distance from said broad base to said tip, is within a range from about 50 $\mu$m to about 100 $\mu$m.

3. The hollow microneedle of claim 1, wherein a height of each microneedle, which is defined as a distance from said broad base to said tip, is substantially less than a width of said broad base.

4. The hollow microneedle of claim 1, wherein said hollow microneedle comprises silicon.

5. Apparatus for conveying a fluid transcutaneously, comprising:
   (a) a substrate, said substrate comprising at least one inlet, and a plurality of outlets in fluid communication with said at least one inlet; and
   (b) a plurality of microneedles arranged in an array and extending substantially outwardly from said substrate, each microneedle including:

(i) a generally conical-shaped body having a beveled, non-coring tip, said tip being sharp and able to pierce tissue;

(ii) said conical body further having a broad base formed of the substrate at an opposite end from the tip; and (iii) a fluid channel extending through the conical-shaped body, providing fluid communication between one of the outlets disposed said broad base is formed from the substrate and said tip;

(c) wherein the conical body has a concave curved surface defined adjacent the tip.

6. The apparatus of claim 5, wherein a height of each microneedle, which is defined as a distance from said broad base to said tip, is within a range from about 50 $\mu$m to about 100 $\mu$m.

7. The apparatus of claim 5, wherein a height of each microneedle, which is defined as a distance from said broad base to said tip, is substantially less than a width of said broad base.

8. The apparatus of claim 5, wherein at least one of said substrate and the microneedles comprises silicon.

9. The apparatus of claim 5, wherein said array of the microneedles is integrally formed from said substrate.

10. The hollow microneedle of claim 1, wherein the curved surface surrounds the beveled tip.

11. An apparatus in accordance with claim 5 produced by a process comprising the steps of:

(a) providing a silicon substrate;

(b) preparing a dotted mask on an upper surface of said silicon substrate, such that openings in said dotted mask correspond to desired locations for said hollow microneedles in the array;

(c) etching said silicon substrate so as to form a plurality of fluid channels that extend substantially through said silicon substrate;

(d) forming a nitride mask such that said nitride mask covers areas in which no nitride layer is desired;

(e) forming a nitride layer, such that said nitride layer is deposited on the substrate in the areas not covered by the nitride mask;

(f) removing said nitride mask;

(g) performing a bevel etch upon said substrate, thereby forming an array of blunt, angular microneedles;

(h) removing said nitride layer; and (i) performing a rounding etch to round and sharpen said blunt angular microneedles, thereby completing said array of hollow microneedles.

12. The apparatus of claim 5, wherein the curved surface surrounds the beveled tip.

13. A hollow microneedle in accordance with claim 1, formed by a process comprising the steps of:

(a) providing a substrate comprising one of silicon and polysilicon;

(b) forming a fluid channel within said substrate, such that said fluid channel passes through said substrate;

(c) removing a substantial portion of said substrate, thereby leaving a remainder, said remainder completely circumferentially surrounding said fluid channel and defining a generally conical shape, such that said fluid channel is generally disposed along a central axis of the conical shape;

(d) wherein the step of removing a substantial portion of said substrate comprises the step of beveling a tip of said conical shape so as to form a beveled, non-coring tip for said microneedle;

(e) wherein the step of forming a fluid channel comprises the steps of:

(1) forming a first mask;

(2) etching the substrate through an orifice formed in the first mask to form said fluid channel; and (3) removing said first mask;

(f) wherein the step of removing a substantial portion of said substrate comprises the steps of:

(1) forming a second mask;

(2) depositing a nitride layer;

(3) removing said second mask; and (4) isotropic etching said substrate to remove a substantial portion of said substrate and to form a concave curved surface adjacent to the beveled tip.

* * * * *